United States Patent
Paliwal et al.

(10) Patent No.: US 11,766,419 B2
(45) Date of Patent: Sep. 26, 2023

(54) MEBEVERINE AS SOLUBLE EPOXIDE HYDROLASE INHIBITOR

(71) Applicant: Banasthali Vidyapith, Banasthali (IN)

(72) Inventors: Sarvesh Paliwal, Banasthali (IN); Swapnil Sharma, Banasthali (IN); Neetika Tripathi, Banasthali (IN); Kanika Verma, Banasthali (IN); Swati Paliwal, Banasthali (IN)

(73) Assignee: Banasthali Vidyapith, Banasthali (IN)

( * ) Notice: Subject to any disclaimer, the term of this patent is extended or adjusted under 35 U.S.C. 154(b) by 290 days.

(21) Appl. No.: 17/144,471

(22) Filed: Jan. 8, 2021

(65) Prior Publication Data

US 2022/0218648 A1    Jul. 14, 2022

(51) Int. Cl.
| | | |
|---|---|---|
| *A61K 31/245* | (2006.01) | |
| *A61P 3/06* | (2006.01) | |
| *A61P 9/12* | (2006.01) | |
| *A61K 9/20* | (2006.01) | |

(52) U.S. Cl.
CPC ............. *A61K 31/245* (2013.01); *A61K 9/20* (2013.01); *A61P 3/06* (2018.01); *A61P 9/12* (2018.01)

(58) Field of Classification Search
CPC ................ A61K 31/245; A61P 3/06
See application file for complete search history.

(56) References Cited

U.S. PATENT DOCUMENTS

| | | | |
|---|---|---|---|
| 2010/0135956 A1* | 6/2010 | Gant ................ | A61K 31/675 514/6.9 |
| 2013/0017262 A1* | 1/2013 | Mullen ............. | A61K 31/196 514/567 |
| 2013/0022676 A1* | 1/2013 | Mullen ............. | A61K 31/437 514/249 |
| 2013/0022677 A1* | 1/2013 | Mullen ............. | A61P 13/12 424/472 |
| 2020/0121657 A1* | 4/2020 | Pandey ............. | C07D 471/04 |

OTHER PUBLICATIONS

Karaya O.V, Method of Treatment of Chronic Acalculous Cholecystitis With Hyperkinetic Type of Gallbladder Diskinesis in Combination With Hypertension, Abstracts of the scientific-practical conference with international participation, Ukraine, Kharkiv, p. 7-8, May 22, 2020.*
Nagamani, Data Science Driven Drug Repurposing for Metabolic Disorders, In Silico Drug Design, 2019, available at https://www.sciencedirect.com/topics/pharmacology-toxicology-and-pharmaceutical-science/metabolic-disorder#:~:text=Metabolic%20disorders%20can%20be%20broadly,or%20abnormalities%20in%20their%20function.*
Maron, Contemporary Definitions and Classification of the Cardiomyopathies, Circulation, vol. 113, Issue 14, Apr. 11, 2006; pp. 1807-1816.*

* cited by examiner

*Primary Examiner* — Svetlana M Ivanova
(74) *Attorney, Agent, or Firm* — Lucas & Mercanti, LLP

(57) ABSTRACT

The present invention relates to a method of using Mebeverine as an sEH inhibitor. The present invention also provides a method of treating metabolic and cardiovascular disorders using Mebeverine.

9 Claims, 12 Drawing Sheets

MEBEVERINE AS SOLUBLE EPOXIDE HYDROLASE INHIBITOR

BACKGROUND

Soluble epoxide hydrolases (sEH) are bifunctional enzymes and are found in both the cytosol and peroxisomes. They bind to specific epoxides and convert them to the corresponding diols. It is well known that enzyme sEH metabolizes epoxyeicosatrienoic acids (EETs) to less active dihydroxyeicosatrienoic acids (DHETs). This conversion reaction reduces the beneficial cardiovascular activities of EETs, such as vasodilation, anti-inflammatory action and lipid lowering ability. Thus, treatment with sEH inhibitors can be considered as a rational therapy in the treatment of various metabolic and cardiovascular disorders such as hypertension, hyperlipidemia, blood glucose levels, cardiac hypertrophy, atherosclerosis and other related diseases.

There are many documents which disclose various novel sEH inhibitors and their use in the management of cardiovascular and metabolic disorders.

U.S. Pat. No. 6,531,506B1 discloses a method of treating hypertension using an inhibitor of epoxide hydrolase.

US20030119900 discloses a method of treating hypertension using certain urea, amide, and carbamate compounds as an inhibitor of epoxide hydrolase.

WO2006121684 discloses a method of treating cardiovascular diseases using acyl hydrazones compounds as soluble epoxide hydrolase inhibitors.

WO2007106525 discloses certain piperidinyl, indolyl, pyrinidyl, morpholinyl and benzimidazolyl urea derivatives as inhibitors of soluble epoxide hydrolase for the treatment of hypertension, inflammations and other diseases.

WO2007043653 discloses certain Benzimidazole-5-carboxamide derivatives as sEH inhibitors and their use in the treatment of hypertension and cardiovascular disease.

WO2008112022 discloses 4-piperidinylurea compounds as soluble epoxide hydrolase inhibitors.

WO2009020960 discloses novel 1,3-substituted urea compounds as inhibitors of soluble epoxide hydrolase and their use in the treatment of sEH-mediated disease or condition.

US20100016310 discloses a method of treating cardiovascular disease using aryl sulfonyl compounds as soluble epoxide hydrolase inhibitors.

Despite being a potential target for the treatment of many metabolic disorders, there is no molecule that can be efficiently used as its inhibitor on a clinical level. It is to be noted that AR9281, a potent and selective sEH inhibitor developed by Arete Therapeutics underwent clinical trials also for the treatment of hypertension and type 2 diabetes. However, much information on the results and further development is not known.

While the literature is replete with novel compounds and possible leads that can be used as sEH inhibitors, the safety and efficacy of these compounds on large scale populations is not yet known and hence their potential use in the management of diseases is still uncertain.

The inventors of the present invention have surprisingly found that Mebeverine, a well-known drug, established in the use for irritable bowel syndrome (IBS), can act as sEH inhibitors and hence can be used for the treatment of conditions mediated by sEH inhibition.

SUMMARY

The present invention discloses Mebeverine as sEH inhibitor.

The present invention relates to methods of using Mebeverine, its pharmaceutically acceptable salts, solvates, tautomers, derivatives, enantiomers, isomers, hydrates, or polymorphs thereof, as sEH inhibitors.

The present invention also relates to a method for the treatment of a sEH inhibition responsive condition using Mebeverine.

The present invention also relates to a method for the treatment of metabolic and cardiovascular disorders.

The present invention also relates to a method for the treatment of metabolic and cardiovascular disorders such as hypertension, hyperlipidemia, increased blood glucose levels, cardiac hypertrophy and atherosclerosis, using Mebeverine.

The present invention also provides pharmaceutical compositions comprising Mebeverine for the treatment of metabolic and cardiovascular disorders such as hypertension, hyperlipidemia, increased blood glucose levels, cardiac hypertrophy and atherosclerosis.

The pharmaceutical composition can comprise, consist essentially of, or consist of mebeverine as the sole active ingredient and one or more pharmaceutically acceptable excipients.

In one embodiment, the mebeverine can be used as a therapeutic agent for one or more of controlling hypertension, lowering lipid levels in serum and reducing the risk of developing metabolic diseases and related diseases. In this embodiment, the mebeverine can be in the form of a pharmaceutical composition with one or more pharmaceutically acceptable excipients.

In another embodiment, the mebeverine can be administered for the property of exhibiting anti-oxidant potential and/or properties. The anti-oxidant potential and/or properties can be characterized as being a strong potential and/or property.

BRIEF DESCRIPTION OF THE DRAWINGS

FIG. 3($b$): Effect of Mebeverine on diastolic pressure in angiotensin-II induced hypertensive rats; FIG. 3($c$): Effect of Mebeverine on mean arterial pressure (MAP) in angiotensin-II induced hypertensive rats.

FIG. 4($b$): Effect of Mebeverine on diastolic pressure in DOCA-induced hypertensive rats; FIG. 4($c$): Effect of Mebeverine on MAP in DOCA-induced hypertensive rats.

FIG. 5($b$): Effect of mebeverine on TBARS assay in heart tissue in DOCA-induced hypertensive rats.

FIG. 6($b$): Effect of mebeverine on SOD assay in heart tissue in DOCA-induced hypertensive rats.

FIG. 7($b$): Effect on HDL; FIG. 7($c$): Effect on Cholesterol; FIG. 7($d$): Effect on LDL; FIG. 7($e$): Effect on VLDL.

DETAILED DESCRIPTION

Figure 1:
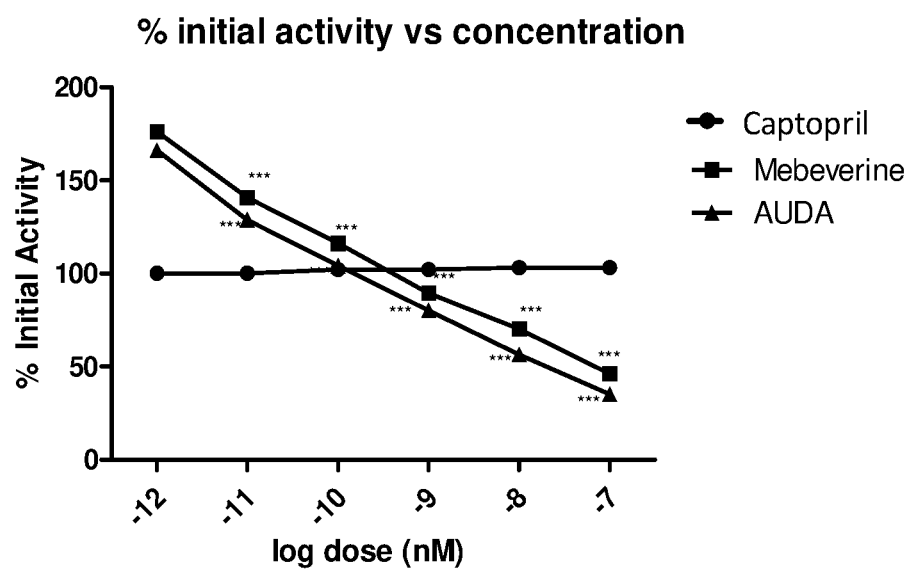
FIG. 1: In-vitro sEH inhibitory activity of Mebeverine and AUDA.

Soluble epoxide hydrolase (sEH) inhibitors are compounds which inhibit the activity of epoxide hydrolase enzyme and block the resulting biochemical activities. These can be used for the treatment of various cardiovascular and metabolic diseases.

The inventors of the present invention have surprisingly found that Mebeverine, a well known anti-spasmodic agent, acts as sEH inhibitor.

Definitions:

As used herein, "Mebeverine" refers to compounds of Formula (I), its pharmaceutically acceptable salts, solvates, tautomers, derivatives, enantiomers, isomers, hydrates, prodrugs or polymorphs thereof.

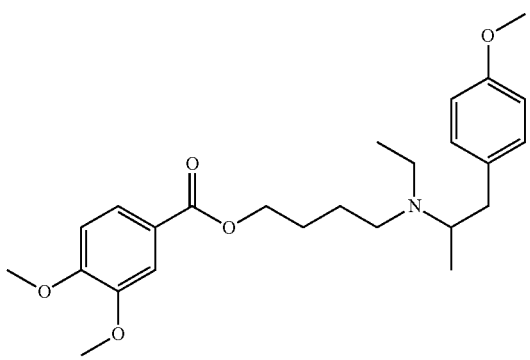

Formula (I)

As used herein, the term "pharmaceutically acceptable salts" refers to salts prepared from pharmaceutically acceptable non-toxic acids such as hydrochloric, hydrobromic, phosphoric, and sulfuric acids. A most preferred salt is the hydrochloride salt (Mebeverine hydrochloride).

As used herein the term "therapeutically effective amount", refers to the amount of Mebeverine sufficient to produce the desired effect when administered by oral, topical, parenteral, transdermal, transmucosal, intranasal, rectally or vaginal route. The preferred therapeutically effective amount is between 0.01 and 100 mg/kg body weight of the subject, e.g., 0.02, 0.03, 0.04, 0.05, 0.06, 0.07, 0.08, 0.09, 0.10, 0.20, 0.30, 0.40, 0.50, 0.60, 0.70, 0.80, 0.90, 1, 2, 3, 4, 5, 6, 7, 8, 9, 10, 20, 30, 40, 50, 60, 70, 80, 90 mg/kg body weight, and values between those listed.

The term "sEH inhibition responsive condition" refers to metabolic and cardiovascular disorders such as hypertension, hyperlipidemia, increased blood glucose levels, cardiac hypertrophy and atherosclerosis.

In one embodiment, the present invention relates to methods of using Mebeverine, its pharmaceutically acceptable salts, solvates, tautomers, derivatives, enantiomers, isomers, hydrates, or polymorphs thereof, as sEH inhibitors.

In one embodiment, the present invention also relates to a method for the treatment of a sEH inhibition responsive condition using Mebeverine.

sEH responsive conditions that can be treated using Mebeverine as per the present invention are selected from metabolic and cardiovascular disorders.

In one embodiment the metabolic and cardiovascular disorders includes hypertension, hyperlipidemia, increased blood glucose levels, cardiac hypertrophy and atherosclerosis.

In another embodiment the present invention also provides pharmaceutical compositions comprising Mebeverine for the treatment of metabolic and cardiovascular disorders such as hypertension, hyperlipidemia, increased blood glucose levels, cardiac hypertrophy, and atherosclerosis.

The composition of the present invention can be administered by oral, topical, parenteral, transdermal, transmucosal, intranasal, rectally or vaginal route. The dosage form can be immediate or sustained release.

The dosage form suitable for the present invention is selected from but not limited to oral dosage forms such as tablets, capsules, caplets, pills, troches, powders, syrups, elixirs, suspensions, solutions, emulsions, sachets, and cachets, parenteral dosage forms such as sterile solutions, suspensions, and powders for reconstitution; transdermal dosage forms such as transdermal patches; rectal dosage forms such as suppositories; inhalation such as aerosols and solutions; and topical dosage forms such as creams, ointments, lotions, solutions, pastes, sprays, foams, and gels.

For being an effective sEH inhibitor, Mebeverine can be in a therapeutically effective amount. The therapeutically effective amount ranges between 0.01 to 30 mg/kg, e.g., 0.02, 0.03, 0.04, 0.05, 0.06, 0.07, 0.08, 0.09, 0.10, 0.20, 0.30, 0.40, 0.50, 0.60, 0.70, 0.80, 0.90, 1, 2, 3, 4, 5, 6, 7, 8, 9, 10, 20 mg/kg, and values between those listed. In a preferred embodiment it is used in an amount of about 5-25 mg/kg. The dose can vary from 100-600 mg/day in divided doses, e.g., 100 mg, 125 mg, 150 mg, 175 mg, 200 mg, 250 mg, 300 mg, 400 mg, 500 mg.

In one embodiment of the present invention, the dosage form is a tablet comprising:
  Mebeverine, or a pharmaceutically acceptable salt thereof in an amount of about 90-98% by weight of the tablet;
  at least one binding agent in an amount of about 1-5% by weight of the tablet; and
  at least one lubricant in an amount of about 0.1-2% by weight of the tablet.

The pharmaceutical composition of the invention may further comprise bulking agents, disintegrating agents, antiadherents, glidants, lubricants, colorants, binding agents and other fillers.

The bulking agents suitable for use in the present invention can be microcrystalline cellulose, dicalcium phosphate, calcium sulfate, starch confectioner's sugar, compressible sugar, dextrates, dextrin, dextrose, lactose, mannitol, microcrystalline cellulose, powdered cellulose, sorbitol, and sucrose.

The disintegrating agents suitable for use in the present invention can be microcrystalline cellulose, starches, crospovidone, sodium starch glycolate, and croscarmellose sodium.

Antiadherents and glidants suitable for use in the present invention can be talc, corn starch, silicon dioxide, sodium lauryl sulfate, and metallic stearates.

Lubricants suitable for use in the present invention can be magnesium stearate, calcium stearate, sodium stearate, stearic acid, sodium stearyl fumarate, sterotex, talc, colloidal silica dioxide, glyceryl behenate, stearic acid, hydrogenated castor oil, glyceryl monostearate and sodium stearyl fumarate and waxes.

Binding agents suitable for use in the present invention can be polyvinyl pyrrolidone, starch, methyl cellulose, hydroxypropyl methylcellulose, carboxymethyl cellulose.

EXAMPLES

The following examples are given by way of illustration of the present invention and therefore should not be construed to limit the scope of the present invention.

Abbreviations Used:

AUDA: 12-(3adamantan-1-yl-ureido)-dodecanoic acid

AI: Atherogenic index

BP: Blood pressure

CRI: Coronary risk index

DAP: Diastolic arterial pressure

DMSO: Dimethyl sulfoxide

DOCA: Deoxy corticosterone acetate

KCl: Potassium chloride

MAP: Mean arterial pressure

NaCl: Sodium chloride nM: nanomole

PHOME (3-phenyl-cyano 6-methoxy-2-naphthalenyl) methyl ester-2-oxiraneacetic acid SAP: Systolic arterial pressure sEH: soluble epoxide hydrolase

Example 1: In Vitro Assay of Mebeverine as sEH Inhibitor

The inhibitory potential of mebeverine was observed in vitro using a sEH activity assay. 5 µl of PHOME (substrate) was added at different concentrations ($10^{-12}$ to $10^{-7}$ nM) of captopril (does not inhibit sEH), Mebeverine and AUDA (known sEH inhibitor). Hydrolysis of PHOME by sEH results in the release of cyanohydrins that further decomposes to cyanide ion and 6-methoxy-2-naphthaldehyde (highly fluorescent). The fluorescence was analyzed at an excitation and emission wavelength of 330 nm and 465 nm respectively. It was observed that the enzyme activity of sEH decreased with the increase in concentrations of both the mebeverine and AUDA This shows that mebeverine is a potent inhibitor of sEH enzyme and it inhibits the activity of the enzyme in a dose-dependent manner ($10^{-12}$ to $10^{-7}$ nM). Captopril showed 100% sEH activity. Interestingly, the inhibitory activity of mebeverine was found comparable to the known standard inhibitor AUDA. Mebeverine exhibited $IC_{50}$ of 3.9 followed by captopril with 693.0 that were comparable to the standard AUDA with $IC_{50}$ of 3.5. The results are tabulated below and have been plotted in FIG. 1.

TABLE 1

| $IC_{50}$ of Mebeverine and AUDA | |
|---|---|
| Compounds | $IC_{50}$ (nM) |
| Mebeverine | 3.9 |
| AUDA | 3.5 |
| Captopril | 693.0 |

Example 2: Ex-Vivo Antihypertensive Studies on Isolated Rat Aortic Strip

Figure 2:
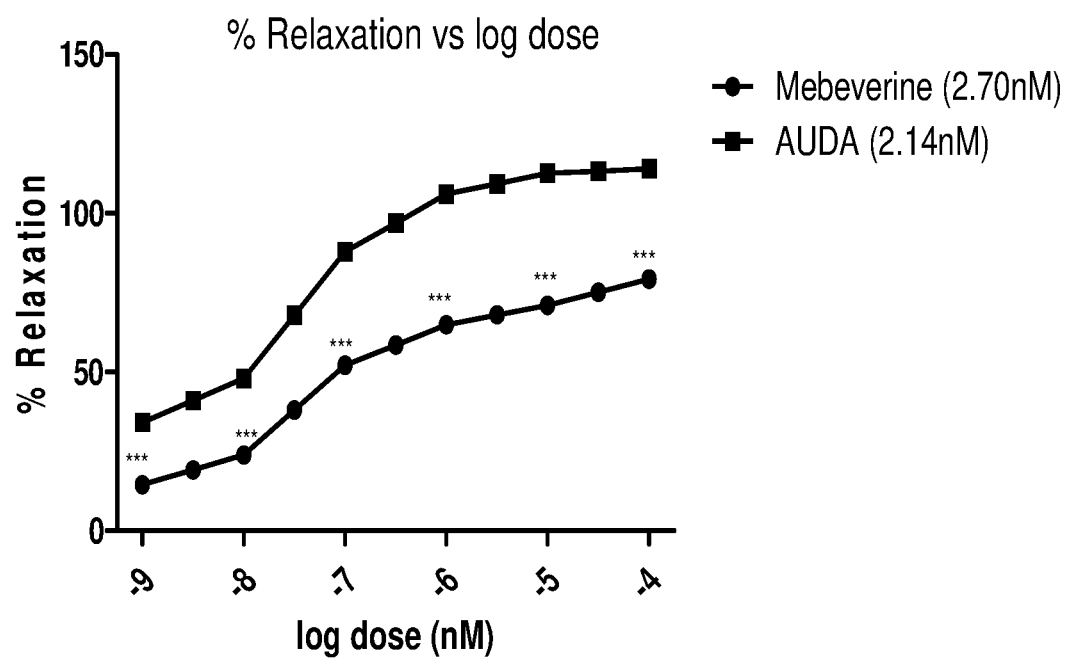
FIG. 2: Effect of Mebeverine on isolated aortic strip (ex-vivo study).

Aortic rings were suspended in organ baths containing a modified Krebs buffer and bubbled with a mixture of 95% $O_2$/5% $CO_2$. Rings were connected to an isometric force transducer, resting tension was set to 5 g and constricted with 80 mmol KCl. The relaxation of these pre-constricted aortic trips at different concentrations of mebeverine ($10^{-9}$-$10^{-4}$ nM) are tabulated in Table 2 and plotted in FIG. 2.

TABLE 2

| Effect of Mebeverine on relaxation of pre-constricted aortic trips | |
|---|---|
| Mebeverine conc (nM) | % relaxation |
| $10^{-9}$ | 14.5 |
| $10^{-8}$ | 23.9 |
| $10^{-7}$ | 52.2 |
| $10^{-6}$ | 64.9 |
| $10^{-5}$ | 71.1 |
| $10^{-4}$ | 79.3 |

It was observed that mebeverine successfully increased the percentage relaxation in the rings in a dose dependent manner ($10^{-9}$ nM to $10^{-4}$ nM). The maximal relaxant effect for Mebeverine was 79.3±0.01% at $10^{-4}$ nM.

Example 3: Effect of Mebeverine on Hypertension

Example 3A: Effect on Angiotensin II Induced Hypertension

Figure 3:
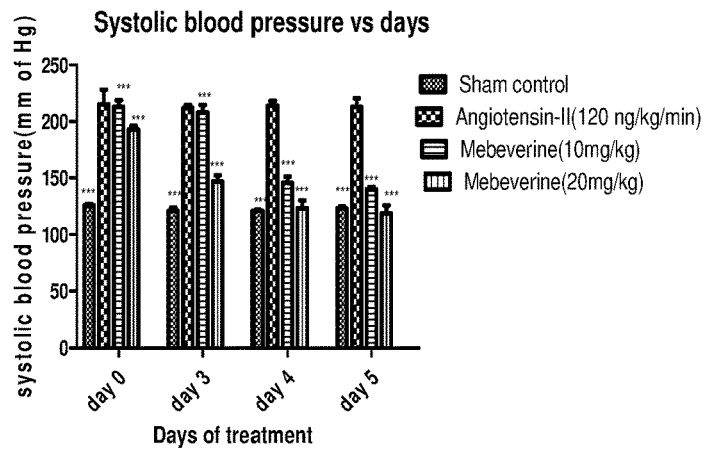
FIG. 3($a$): Effect of Mebeverine on systolic pressure in angiotensin-II induced hypertensive rats.
Figure 3:
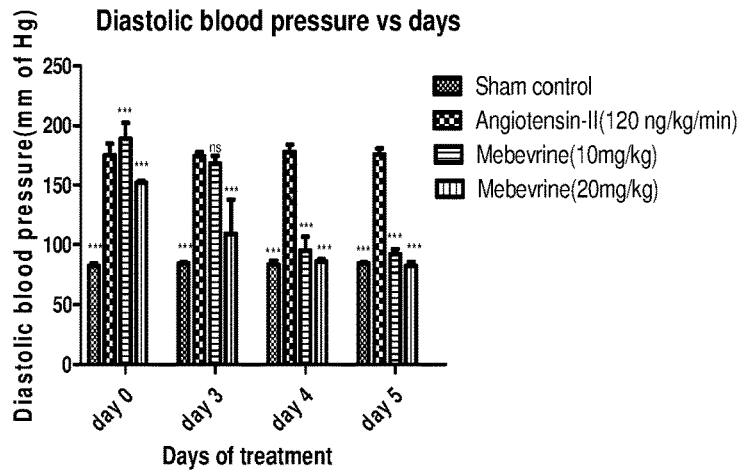
Figure 3:
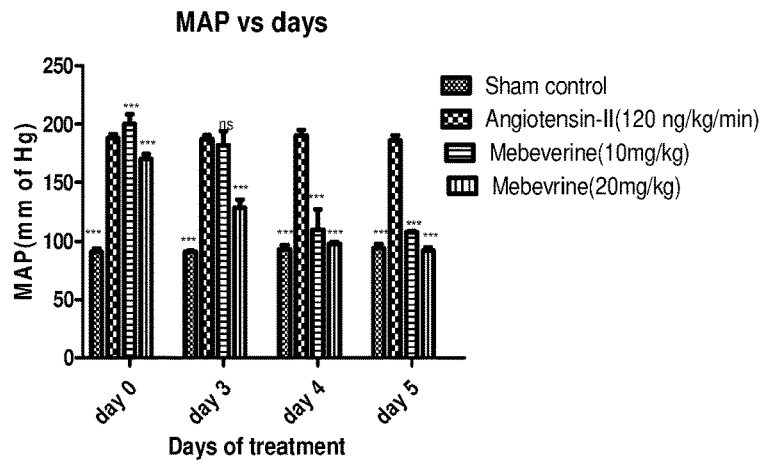

Wistar albino male rats were divided into four experimental groups (I, II, III and IV). Groups II-IV were infused with Angiotensin II at a continuous rate via subcutaneously implanted osmotic mini pump for 7 days. After induction of high blood pressure, (>140/90 mm of Hg), Groups III and IV were administered with mebeverine twice daily for five consecutive days at 10 mg/kg and 20 mg/kg doses respectively. At the end of this experimental period SAP, DAP and MAP were measured. The results are tabulated below in Tables 3A, 3B, and 3C, respectively, and are plotted in FIGS. 3a, 3b and 3c. The results clearly show that Mebeverine reduces the high blood pressure consistently in a consistent manner at both 10 mg/kg and 20 mg/kg ($P<0.001$).

TABLE 3A

Effect of Mebeverine on Angiotensin II induced hypertension (SAP)

| | | SAP (mm Hg) | | | |
|---|---|---|---|---|---|
| Group | Treatment | D 0 | D 3 | D 4 | D 5 |
| I | Sham Control | 126 ± 1.03 | 121 ± 2.82 | 121 ± 1.08 | 123 ± 2.08 |
| II | Angiotensin II (120 ng/kg/min) | 215 ± 13.43 | 212 ± 2.83 | 214 ± 4.35 | 213 ± 3.33 |
| III | Mebeverine (10 mg/kg) | 213 ± 6.360 | 208 ± 6.970 | 146 ± 5.370 | 140 ± 2.120 |
| IV | Mebeverine (20 mg/kg) | 193 ± 3.530 | 147 ± 5.600 | 123 ± 7.28 | 119 ± 7.07 |

TABLE 3B

Effect of Mebeverine on Angiotensin II induced hypertension (DAP)

| | | DAP (mm Hg) | | | |
|---|---|---|---|---|---|
| Group | Treatment | D 0 | D 3 | D 4 | D 5 |
| I | Sham Control | 82 ± 2.09 | 84 ± 1.08 | 83 ± 3.53 | 84 ± 1.08 |
| II | Angiotensin II (120 ng/kg/min) | 175 ± 9.89 | 174 ± 3.53 | 178 ± 6.11 | 176 ± 4.70 |
| III | Mebeverine (10 mg/kg) | 189 ± 13.43 | 168 ± 6.86 | 95 ± 11.70 | 92 ± 4.24 |
| IV | Mebeverine (20 mg/kg) | 152 ± 1.40 | 109 ± 28.80 | 86 ± 1.70 | 82 ± 3.53 |

TABLE 3C

Effect of Mebeverine on Angiotensin II induced hypertension (MAP)

| | | MAP (mm Hg) | | | |
|---|---|---|---|---|---|
| Group | Treatment | D 0 | D 3 | D 4 | D 5 |
| I | Sham Control | 91 ± 2.72 | 91 ± 1.08 | 93 ± 3.53 | 94 ± 3.53 |
| II | Angiotensin II (120 ng/kg/min) | 188 ± 3.53 | 187 ± 3.53 | 190 ± 5.13 | 186 ± 4.24 |
| III | Mebeverine (10 mg/kg) | 200 ± 8.40 | 182 ± 12.02 | 110 ± 16.78 | 108 ± 1.07 |
| IV | Mebeverine (20 mg/kg) | 170 ± 4.30 | 128 ± 7.07 | 98 ± 1.51 | 92 ± 2.82 |

Example 3B: Effect on DOCA Induced Hypertension

Figure 4:
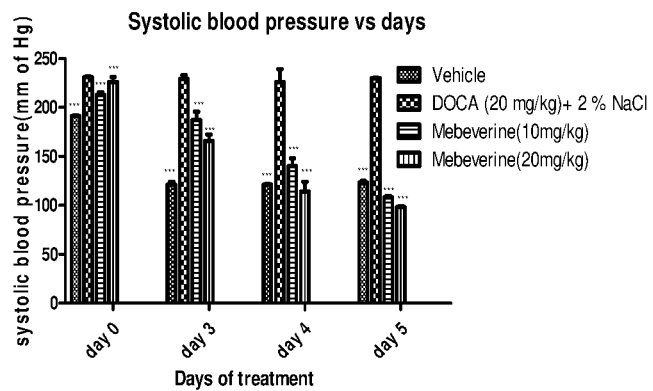
FIG. 4($a$): Effect of Mebeverine on systolic pressure in DOCA-induced hypertensive rats.
Figure 4:
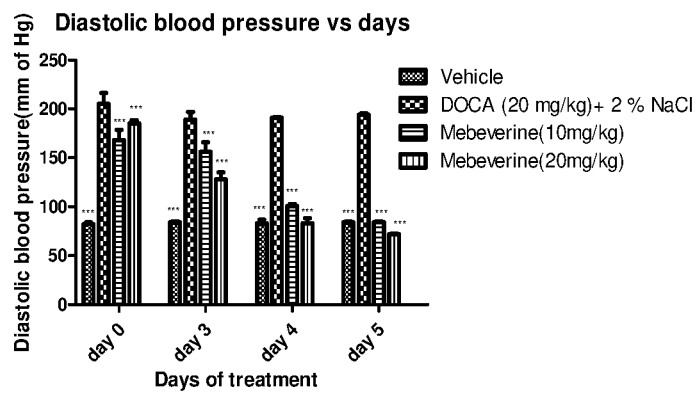
Figure 4:
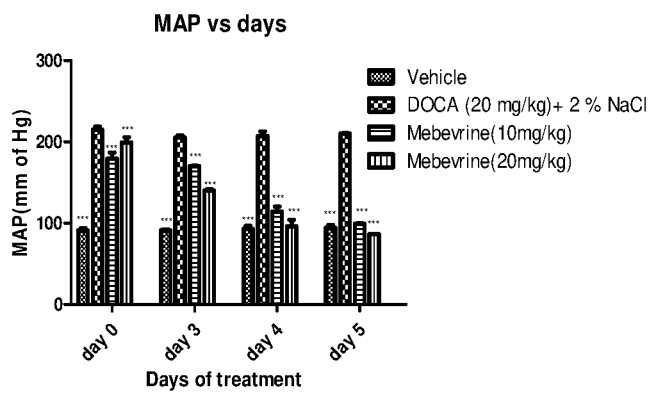

Wistar albino male rats were divided into four experimental groups (I, II, III and IV). Groups (II-IV) were administered with DOCA (20 mg/kg in 5% DMSO) intraperitoneally and drinking water was replaced by 2% NaCl. After induction of high blood pressure, Groups III and IV were treated with 10 mg/kg and 20 mg/kg mebeverine orally, respectively. At the end of this experimental period SAP, DAP and MAP were measured. The results are tabulated below in Tables 4A, 4B and 4C, respectively, and are plotted in FIGS. 4a, 4b and 4c.

TABLE 4A

Experimental design and result of DOCA induced hypertension (SAP)

| | | SAP (mm Hg) | | | |
|---|---|---|---|---|---|
| Group | Treatment | D 0 | D 3 | D 4 | D 5 |
| I | Control | 121 ± 1.03 | 121 ± 2.82 | 121 ± 1.08 | 123 ± 2.08 |
| II | DOCA (20 mg/kg, I.P.) + 2% NaCl | 231 ± 0.707 | 229 ± 4.09 | 226 ± 13.30 | 230 ± 0.70 |
| III | Mebeverine (10 mg/kg) | 213 ± 2.82 | 187 ± 8.48 | 140 ± 8.00 | 108 ± 1.41 |
| IV | Mebeverine (20 mg/kg) | 226 ± 4.94 | 166 ± 6.36 | 114 ± 10.01 | 98 ± 1.09 |

TABLE 4B

Experimental design and result of DOCA induced hypertension (DAP)

| | | DAP (mm Hg) | | | |
|---|---|---|---|---|---|
| Group | Treatment | D 0 | D 3 | D 4 | D 5 |
| I | Control | 82 ± 2.09 | 84 ± 1.08 | 83 ± 3.53 | 84 ± 1.08 |
| II | DOCA (20 mg/kg, I.P.) + 2% NaCl | 205 ± 11.30 | 189 ± 8.08 | 191 ± 0.70 | 194 ± 1.60 |

TABLE 4B-continued

Experimental design and result of DOCA induced hypertension (DAP)

| | | DAP (mm Hg) | | | |
|---|---|---|---|---|---|
| Group | Treatment | D 0 | D 3 | D 4 | D 5 |
| III | Mebeverine (10 mg/kg) | 168 ± 10.60 | 156 ± 9.89 | 101 ± 1.52 | 84 ± 1.06 |
| IV | Mebeverine (20 mg/kg) | 185 ± 3.50 | 128 ± 7.07 | 83 ± 5.13 | 72 ± 0.70 |

TABLE 4C

Experimental design and result of DOCA induced hypertension (MAP)

| | | MAP (mm Hg) | | | |
|---|---|---|---|---|---|
| Group | Treatment | D 0 | D 3 | D 4 | D 5 |
| I | Control | 91 ± 2.72 | 91 ± 1.08 | 93 ± 3.53 | 94 ± 3.53 |
| II | DOCA (20 mg/kg, I.P.) + 2% NaCl | 215 ± 3.53 | 205 ± 2.82 | 207 ± 5.65 | 210 ± 0.84 |
| III | Mebeverine (10 mg/kg) | 179 ± 7.63 | 170 ± 0.52 | 114 ± 6.08 | 99 ± 0.77 |
| IV | Mebeverine (20 mg/kg) | 199 ± 6.54 | 140 ± 1.71 | 96 ± 7.57 | 86 ± 0.63 |

Figure 5:
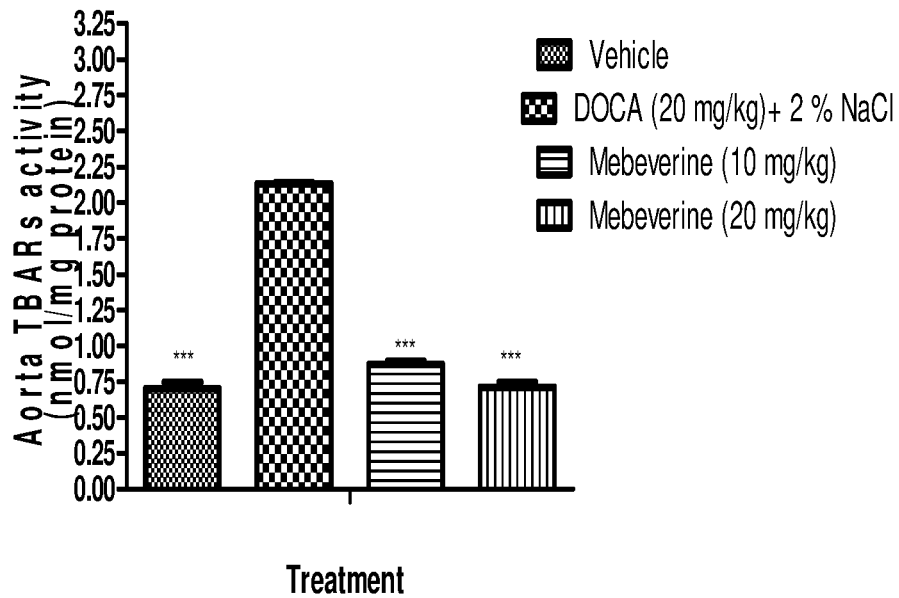
FIG. 5($a$): Effect of mebeverine on TBARS assay in aortic tissue in DOCA-induced hypertensive rats.
Figure 5:
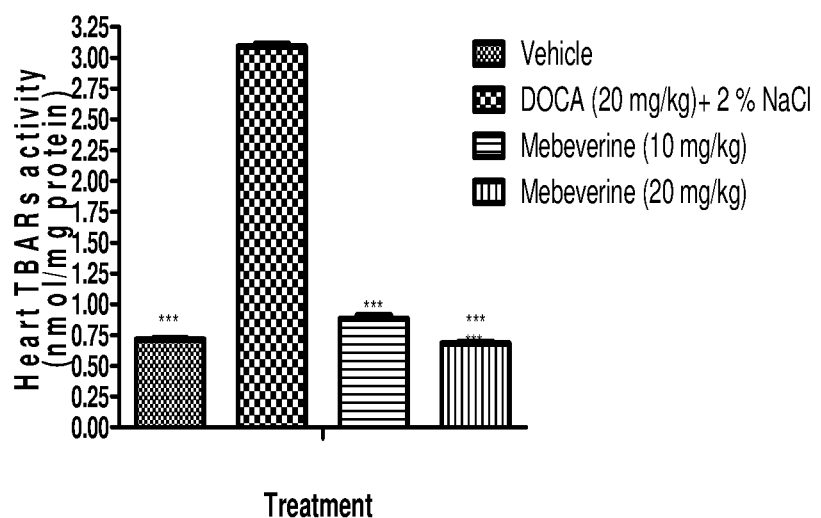
Figure 6:
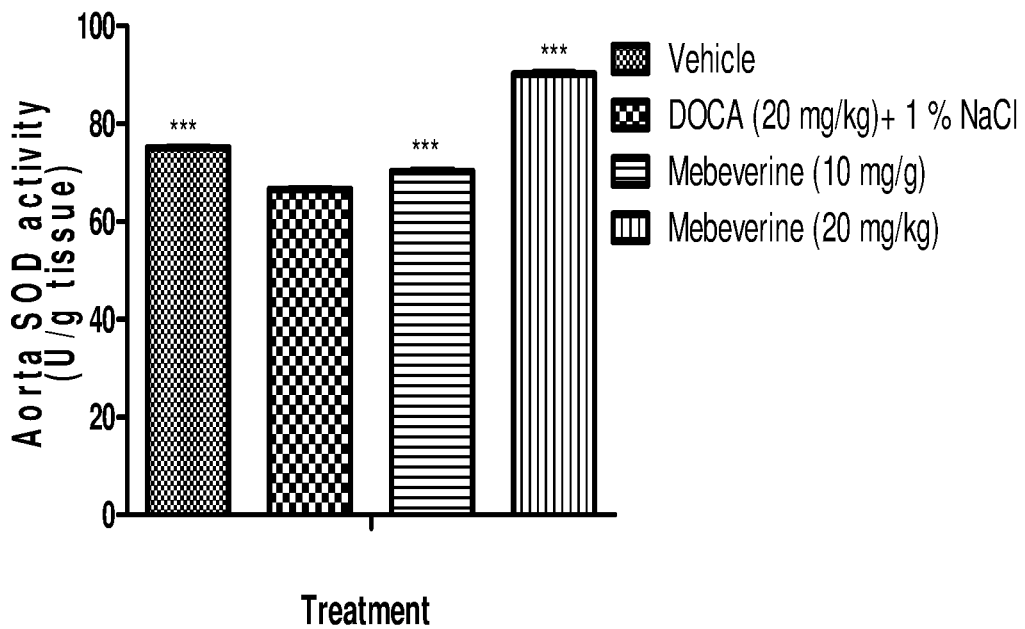
FIG. 6($a$): Effect of mebeverine on SOD assay in aortic tissue in DOCA-induced hypertensive rats.
Figure 6:
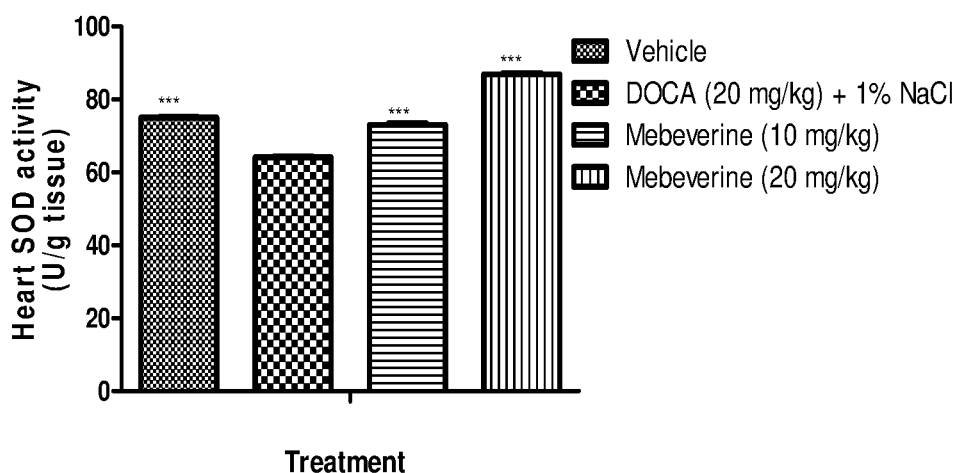

Additionally, the levels of oxidative stress biomarkers, superoxide dismutase (SOD) and thiobarbituric acid (TBARs)s in heart and aortic tissue were also measured (Cayman commercial kit). The results are tabulated in Table 5 and plotted in FIGS. 5a and 5b (TBAR level) and 6a and 6b (SOD level).

TABLE 5

SOD and TBAR level in DOCA induced hypertension

| | | RESULT | | | |
|---|---|---|---|---|---|
| | | SOD Level (U/g tissue) | | TBAR level (nmol/mg protein) | |
| Group | Treatment | Aortic tissue | Heart tissue | Aortic tissue | Heart tissue |
| I | Control | 75.00 ± 0.23 | 75.00 ± 0.23 | 0.70 ± 0.04 | 0.71 ± 0.01 |
| II | DOCA (20 mg/kg, I.P.) + 2% NaCl | 66.52 ± 0.19 | 64 ± 0.29 | 2.31 ± 0.01 | 3.09 ± 0.02 |
| III | Mebeverine (10 mg/kg) | 70.20 ± 0.28 | 73.04 ± 0.29 | 0.87 ± 0.02 | 0.88 ± 0.03 |
| IV | Mebeverine (20 mg/kg) | 90.21 ± 0.21 | 86.24 ± 0.37 | 0.71 ± 0.03 | 0.68 ± 0.01 |

It is clear that Mebeverine shows a significant dose dependent decrease in TBARs concentration and significant dose dependent increase of SOD activity in both aortic and heart tissue.

Example 4: Effect of Mebeverine on Hyperlipidemia

Example 4A: Effect on Triton WR-1339 Induced Hyperlipidemia

Figure 7:
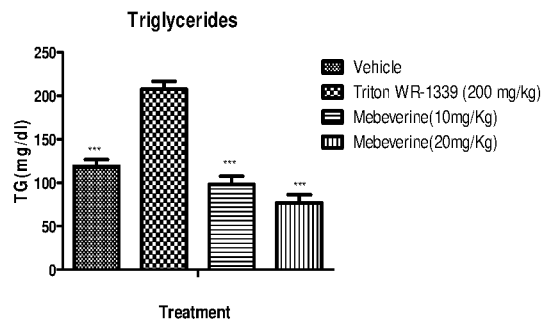
FIG. 7($a$): Effect of mebeverine on lipid profile (Triglyceride, cholesterol, LDL, HDL and VLDL) in triton-induced hyperlipidemic rats. Effect on Triglyceride.
Figure 7:
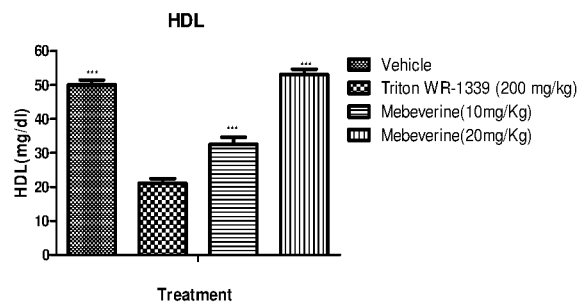
Figure 7:
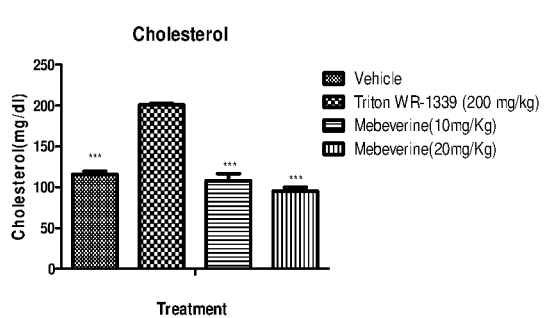
Figure 7:
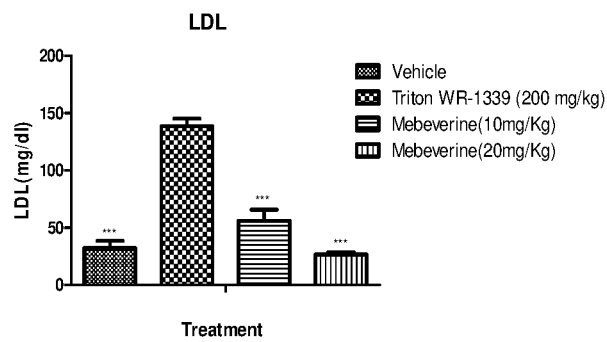
Figure 7:
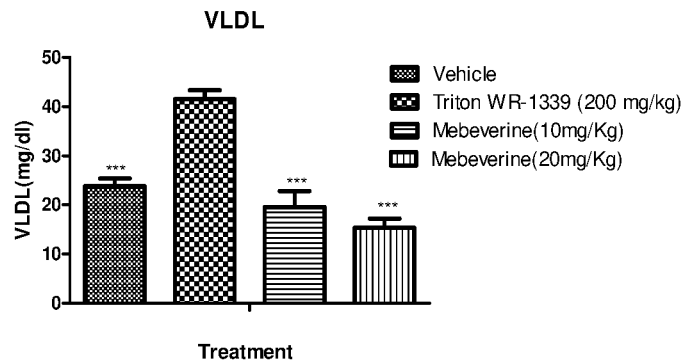
Figure 8:
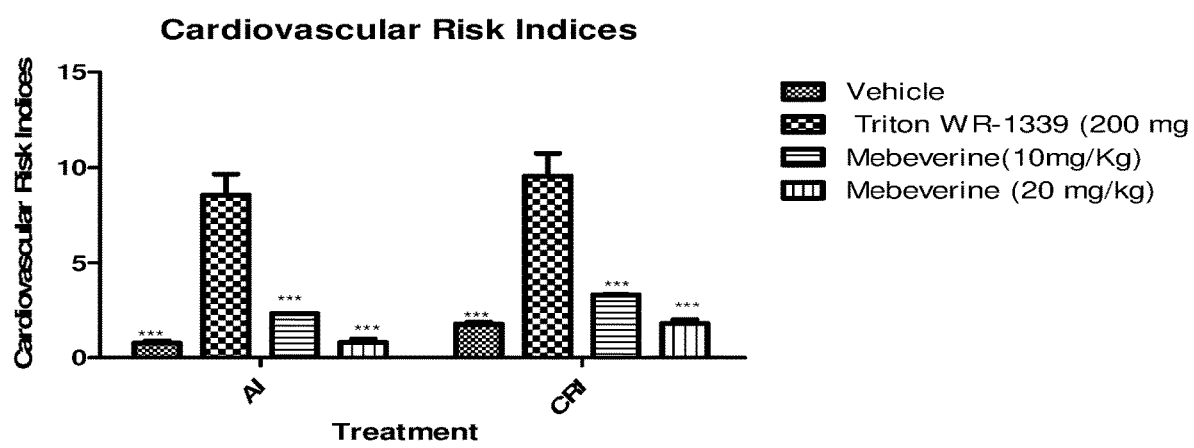
FIG. 8: Effect of mebeverine on the cardiovascular risk indices and atherogenic index in triton-induced hyperlipidemic rats.

Wistar albino male rats were divided into four experimental groups (I, II, III and IV). Groups II-IV were treated with intraperitoneal injection of Triton WR-1339 (200 mg/kg in 2% gum acacia) in 12 h fasted rats to induce hyperlipidemia. Group III and IV were orally administered with Mebeverine twice daily for 3 days at 10 mg/kg and 20 mg/kg. After 48 h, induction of hyperlipidemia blood serum was investigated for total cholesterol and triglycerides. Blood samples were collected from all experimental rats on day 6 (4 days after start of treatment), and, subsequently, serum was separated for analysis of serum lipid profile parameters and CRI/AI. Liver was excised and stored at −80° C. until biochemical parameters in hepatic tissue samples were analysed. The results are tabulated below in Table 6 and plotted in FIGS. 7 (a-e) and 8.

TABLE 6

Effect of mebeverine on lipid profile and CRI/AI on Triton WR-1339 induced hyperlipidaemic rats.

| Group | Treatment | Triglycerides (mg/dl) | Cholesterol (mg/dl) | LDL (mg/dl) | VLDL (mg/dl) | HDL (mg/dl) | CRI | AT |
|---|---|---|---|---|---|---|---|---|
| I | Control | 119.00 ± 7.77 | 116.00 ± 3.53 | 32.20 ± 6.50 | 23.80 ± 1.55 | 50.00 ± 1.41 | 1.76 ± 0.12 | 0.76 ± 0.12 |
| II | Triton WR-1339 (200 | 207.50 ± 9.19 | 201.00 ± 1.42 | 138.00 ± 6.13 | 41.50 ± 1.83 | 21.00 ± 1.41 | 9.57 ± 1.18 | 8.57 ± 1.09 |

TABLE 6-continued

Effect of mebeverine on lipid profile and CRI/AI on Triton WR-1339 induced hyperlipidaemic rats.

| Group | Treatment | Triglycerides (mg/dl) | Cholesterol (mg/dl) | LDL (mg/dl) | VLDL (mg/dl) | HDL (mg/dl) | CRI | AT |
|---|---|---|---|---|---|---|---|---|
| | mg/kg in 2% gum acacia) | | | | | | | |
| III | Mebeverine (10 mg/kg) | 98.00 ± 9.8 | 108.00 ± 8.48 | 55.90 ± 9.75 | 19.60 ± 3.25 | 32.50 ± 2.12 | 3.32 ± 0.02 | 2.32 ± 0.02 |
| IV | Mebeverine (20 mg/kg) | 77.00 ± 9.19 | 95.00 ± 4.94 | 26.90 ± 1.83 | 15.40 ± 1.83 | 53.00 ± 1.59 | 1.79 ± 0.02 | 0.79 ± 0.19 |

It is clear that treatment with mebeverine (10 mg/kg) markedly decreases triglycerides, cholesterol, LDL and VLDL and CRI/AI. It also increases HDL.

Figure 9:
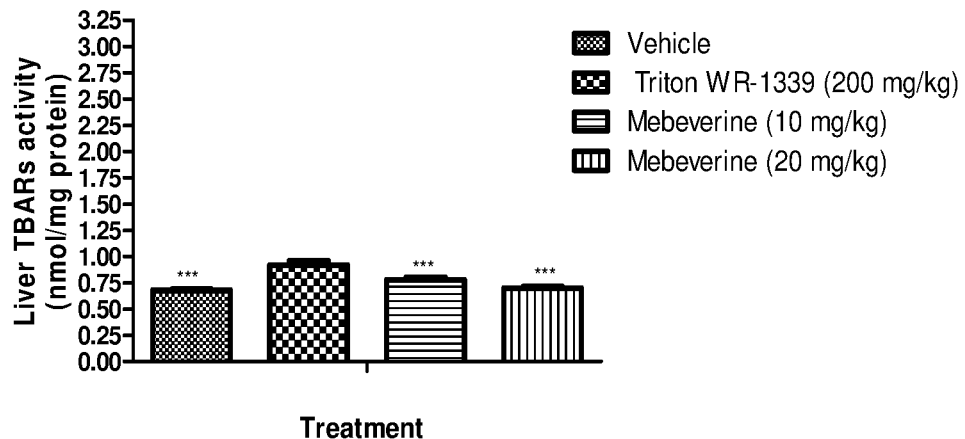
FIG. 9: Effect of mebeverine on TBARs assay in hepatic tissues in triton-induced hyperlipidemic rats.
Figure 10:
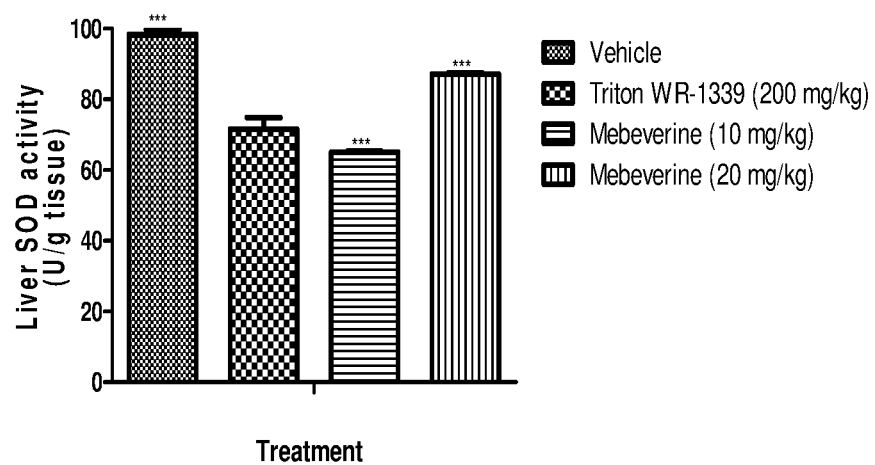
FIG. 10: Effect of mebeverine on SOD assay in hepatic tissue in triton-induced hyperlipidemic rats.

In addition, the effect on oxidative stress markers on hepatic tissue were also observed. The results are shown in Table 7 and plotted in FIGS. 9 and 10.

TABLE 7

Effect of mebeverine on TBAR and SOD level of Triton WR-1339 induced hyperlipidaemic rats.

| Group | Treatment | TBAR(nmol/mg protein) | SOD(U/g protein |
|---|---|---|---|
| I | Control | 0.68 ± 0.00 | 98.42 ± 1.48 |
| II | Triton WR-1339 (200 mg/kg in 2% gum acacia) | 0.92 ± 0.04 | 71.64 ± 3.26 |
| III | Mebeverine (10 mg/kg) | 0.78 ± 0.01 | 65.13 ± 0.22 |
| IV | Mebeverine (20 mg/kg) | 0.70 ± 0.01 | 87.27 ± 0.30 |

Example 4B: Effect on Lipopolysaccharide (LPS)-Induced Hyperlipidemia

Figure 11:
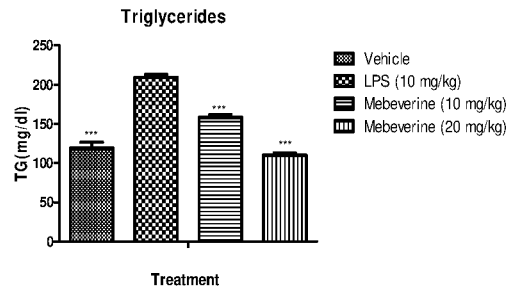
FIG. 11(a), (b), (c), (d) and (e): Effect of mebeverine on the lipid profile in LPS-induced hyperlipidemic rats.
Figure 11:
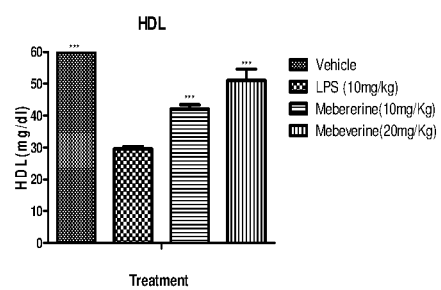
Figure 11:
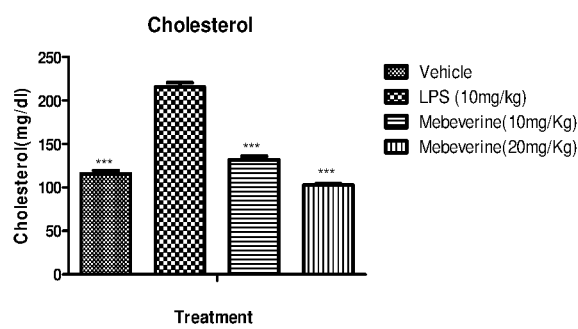
Figure 11:
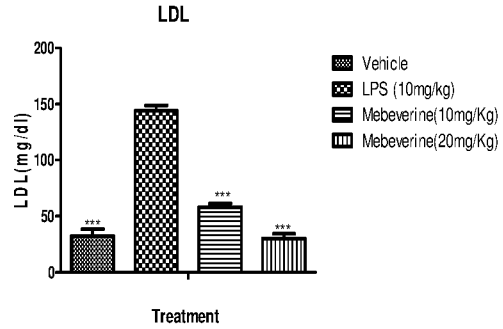
Figure 11:
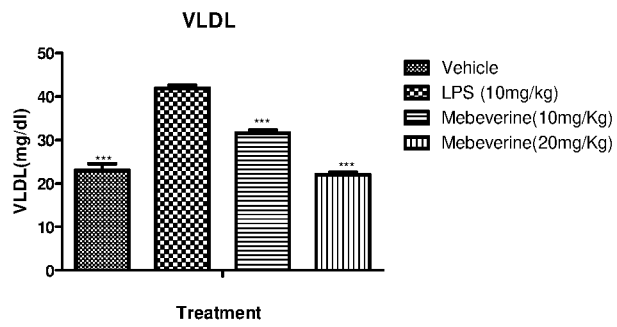
Figure 12:
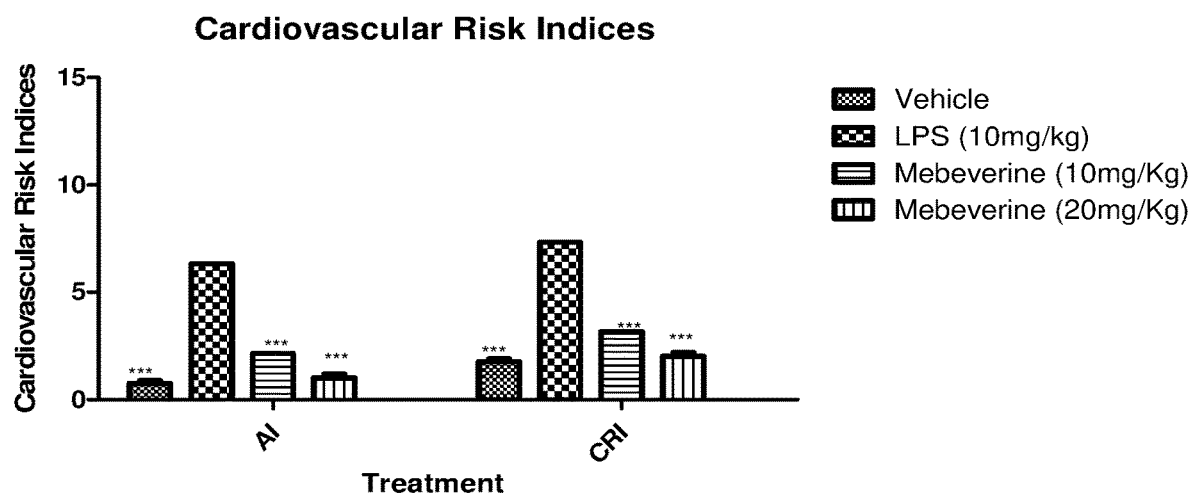
FIG. 12: Effect of mebeverine on the cardiovascular risk indices and atherogenic index in LPS-induced hyperlipidemic rats.

Wistar albino male rats were divided into different experimental groups—Single dose of 10 mg/kg, i.p. of LPS was administered to all the groups (II-IV). After 3 days of induction mebeverine was orally given twice daily for 5 days to groups (III-IV). After last dose, on day 5, blood samples were collected from all experimental rats for analysis of serum lipid profile parameters and CRI/AI. The results are tabulated below in Table 8 and plotted in FIGS. 11 (a-e) and 12. Biochemical estimations in hepatic tissue samples were also analyzed.

Figure 13:
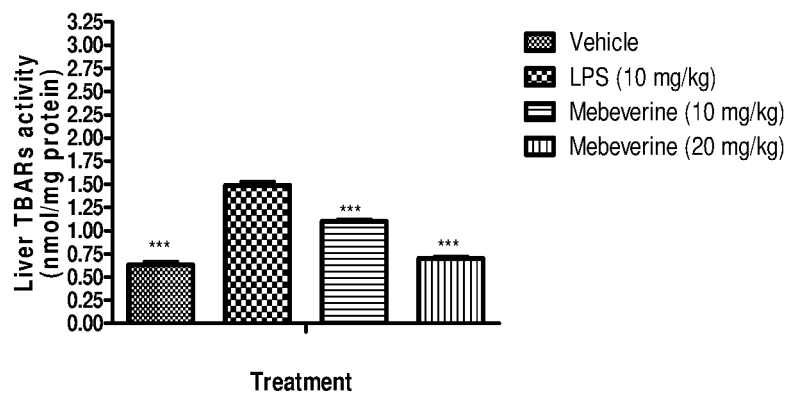
FIG. 13: Effect of mebeverine on TBARs assay in hepatic tissue in LPS-induced hyperlipidemic rats.
Figure 14:
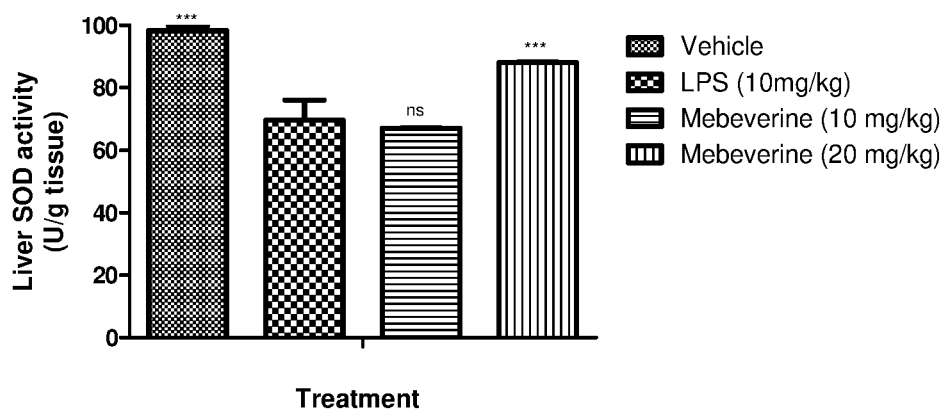
FIG. 14: Effect of mebeverine on SOD assay in hepatic tissue in LPS-induced hyperlipidemic rats.

In addition, the effect on oxidative stress markers on hepatic tissue were also observed as presented below in Table 9. The results are shown in FIGS. 13 and 14.

TABLE 9

Effect of mebeverine on TBAR and SOD level on Lipopolysaccharide (LPS)-induced hyperlipidemic rats.

| Group | Treatment | TBAR (nmol/mg protein) | SOD (U/g protein |
|---|---|---|---|
| I | Control | 0.63 ± 0.03 | 98.42 ± 1.48 |
| II | LPS (10 mg/kg, i.p.) in normal saline | 0.75 ± 0.02 | 69.95 ± 6.37 |
| III | Mebeverine (10 mg/kg) | 1.10 ± 0.01 | 67.13 ± 0.21 |
| IV | Mebeverine (20 mg/kg) | 0.701 ± 0.02 | 74.50 ± 0.15 |

The invention claimed is:

1. A method for treating a sEH inhibition mediated condition in a subject, comprising:
    administering to the subject a therapeutically effective amount of Mebeverine or a salt thereof,
    wherein the sEH inhibition mediated condition the subject is suffering from is hyperlipidemia.

2. The method of claim 1, wherein the Mebeverine is administered by one or more of oral, topical, parenteral, transdermal, transmucosal, intranasal, rectal or vaginal route.

3. The method of claim 1, wherein the therapeutically effective amount is between 0.01 and 100 mg/kg body weight of the subject.

4. The method of claim 1, wherein the mebeverine is in the form of a salt.

TABLE 8

Effect of mebeverine on lipid profile and CRI/AI on Lipopolysaccharide (LPS)-induced hyperlipidaemic rats.

| Group | Treatment | Triglycerides (mg/dl) | Cholesterol (mg/dl) | LDL (mg/dl) | VLDL (mg/dl) | HDL (mg/dl) | CRI | AI |
|---|---|---|---|---|---|---|---|---|
| I | Control | 119.00 ± 7.77 | 116.00 ± 3.53 | 32.00 ± 6.50 | 23.00 ± 1.55 | 60.00 ± 1.41 | 1.76 ± 0.12 | 0.76 ± 0.12 |
| II | LPS (10 mg/kg, i.p.) in normal saline | 209.50 ± 3.53 | 215.5 ± 4.94 | 144.1 ± 4.94 | 41.9 ± 0.70 | 29.5 ± 0.70 | 7.30 ± 0.12 | 6.30 ± 1.18 |
| III | Mebeverine (10 mg/kg) | 158.5 ± 3.58 | 132.5 ± 4.24 | 58.3 ± 3.25 | 31.6 ± 0.34 | 42.0 ± 1.41 | 3.14 ± 0.14 | 2.14 ± 0.02 |
| IV | Mebeverine (20 mg/kg) | 110.00 ± 2.82 | 103.50 ± 1.41 | 30.0 ± 3.25 | 22.0 ± 0.56 | 51.00 ± 3.53 | 2.01 ± 0.17 | 1.01 ± 0.17 |

5. The method of claim 4, wherein the salt is one or more of hydrochloride, hydrobromide, phosphate, and sulfate.

6. The method of claim 5, wherein the salt is the hydrochloride salt.

7. The method of claim 1, wherein the mebeverine is administered for lowering lipid levels in serum.

8. The method of claim 1, wherein the mebeverine exhibits strong anti-oxidant potential.

9. The method of claim 3, wherein the therapeutically effective amount is between 10 and 20 mg/kg body weight of the subject.

* * * * *